US00PP26991P2

(12) United States Plant Patent
Shibamichi

(10) Patent No.: US PP26,991 P2
(45) Date of Patent: Aug. 2, 2016

(54) ***CORNUS* PLANT NAMED 'WATASHI NO GINGA'**

(50) Latin Name: ***Cornus hongkongensis* ssp. *melanotricha***
Varietal Denomination: Watashi no Ginga

(71) Applicant: Masashi Shibamichi, Yuki (JP)

(72) Inventor: Masashi Shibamichi, Yuki (JP)

( * ) Notice: Subject to any disclaimer, the term of this patent is extended or adjusted under 35 U.S.C. 154(b) by 91 days.

(21) Appl. No.: 14/121,957

(22) Filed: Nov. 7, 2014

(51) Int. Cl.
*A01H 5/00* (2006.01)

(52) U.S. Cl.
USPC ..... Plt./220

(58) Field of Classification Search
USPC ..... Plt./220
See application file for complete search history.

*Primary Examiner* — Annette Para
(74) *Attorney, Agent, or Firm* — C. A. Whealy

(57) ABSTRACT

A new and distinct cultivar of *Cornus* plant named 'Watashi no Ginga', characterized by its upright and outwardly spreading plant habit; vigorous growth habit; green, yellow green and yellow-colored variegated leaves; single to double-type flowers that are initially light green in color and becoming white in color with development; and good cold hardiness.

3 Drawing Sheets

Botanical classification: *Cornus hongkongensis* ssp. *melanotricha.*

Cultivar designation: 'Watashi no Ginga'.

BACKGROUND OF THE INVENTION

The present invention relates to a new and distinct cultivar of *Cornus* plant, commercially grown as an ornamental evergreen tree, botanically known as *Cornus hongkongensis* ssp. *melanotricha* and hereinafter referred to by the cultivar name 'Watashi no Ginga'.

The new *Cornus* plant is a naturally-occurring branch mutation of an unnamed selection of *Cornus hongkongensis* ssp. *melanotricha*, not patented. The new *Cornus* plant was discovered and selected by the Inventor on a single plant from within a population of plants of the unnamed selection in a controlled outdoor nursery environment in Tsukuba City, Ibaraki Prefecture, Japan in 2004.

Asexual reproduction of the new *Cornus* plant by bud grafting in a controlled environment in Tsukuba City, Ibaraki Prefecture, Japan since 2004 has shown that the unique features of this new *Cornus* plant are stable and reproduced true to type in successive generations.

SUMMARY OF THE INVENTION

Plants of the new *Cornus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Watashi no Ginga'. These characteristics in combination distinguish 'Watashi no Ginga' as a new and distinct *Cornus* plant:

1. Upright and outwardly spreading plant habit.
2. Vigorous growth habit.
3. Green, yellow green and yellow-colored variegated leaves.

4. Single to double-type flowers that are initially light green in color and becoming white in color with development.
5. Good cold hardiness.

Plants of the new *Cornus* differ primarily from plants of the mutation parent selection in the following characteristics:

1. Plants of the new *Cornus* have variegated leaves whereas plants of the mutation parent selection have non-variegated leaves.
2. Flowers of plants of the new *Cornus* are single to double-types whereas flowers of plants of the mutation parent selection are single-types.
3. Flower bracts of plants of the new *Cornus* are initially light green in color becoming white in color with development whereas flower bracts of plants of the mutation parent selection are white in color.

Plants of the new *Cornus* can be compared to plants of *Cornus kousa* 'Satomi', not patented. In side-by-side comparisons, plants of the new *Cornus* differ primarily from plants of 'Satomi' in the following characteristics:

1. Plants of the new *Cornus* are evergreen whereas plants of 'Satomi' are deciduous.
2. Plants of the new *Cornus* have variegated leaves whereas plants of the 'Satomi' have non-variegated leaves.
3. Flowers of plants of the new *Cornus* are single to double-types whereas flowers of plants of 'Satomi' are single-types.
4. Flower bracts of plants of the new *Cornus* are initially light green in color becoming white in color with development whereas flower bracts of plants of 'Satomi' are pink in color.

Plants of the new *Cornus* can be compared to plants of *Cornus hongkongensis* 'Gekko', not patented. In side-by-side comparisons, plants of the new *Cornus* differ primarily from plants of 'Gekko' in the following characteristics:

1. Plants of the new *Cornus* have variegated leaves whereas plants of the 'Gekko' have non-variegated leaves.
2. Flowers of plants of the new *Cornus* are single to double-types whereas flowers of plants of 'Gekko' are single-types.

3. Flower bracts of plants of the new *Cornus* are initially light green in color becoming white in color with development whereas flower bracts of plants of 'Gekko' are white in color.
4. Plants of the new *Cornus* have not been observed to produce fruits and seeds whereas plants of 'Gekko' produce fruits and seeds.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

The photograph on the first sheet comprises a side perspective view of a typical tree of 'Watashi no Ginga' grown in an outdoor nursery.

The photograph on the second sheet is a close-up view of typical leaves of 'Watashi no Ginga'.

The photograph on the third sheet is a close-up view of typical leaves, developing flowers and fully developed flowers of 'Watashi no Ginga'. Plants used for the aforementioned photographs were grown during the spring in ground beds in an outdoor nursery in Yuki City, Ibaraki Prefecture, Japan. Plants were eight years old when the photographs were taken.

DETAILED BOTANICAL DESCRIPTION

The following observations, measurements and values describe plants grown during the winter in ground beds in a polyvinyl-covered greenhouse in Tsukuba City, Ibaraki Prefecture, Japan and under cultural practices typical of commercial *Cornus* production. During the production of the plants, day temperatures averaged 25.6° C. and night temperatures averaged 4.1° C. Plants were seven years old when the description was taken. In the following description, color references are made to The Royal Horticultural Society Colour Chart, 2007 Edition, except where general terms of ordinary dictionary significance are used.

Botanical classification: *Cornus hongkongensis* ssp. *melanotricha* 'Watashi no Ginga'.

Parentage: Naturally-occurring branch mutation of an unnamed selection of *Cornus hongkongensis* ssp. *melanotricha*, not patented.

Grafting information:

*Type*.—Bud grafting.

*Stock*.—Unnamed selection of *Cornus kousa*.

Plant description:

*Plant form and growth habit*.—Upright evergreen tree; roughly ovate in overall shape; vigorous growth habit.

*Plant height*.—About 3 meters to 5 meters.

*Plant width* (*spread*).—About 2 meters.

*Trunk circumference*.—About 26.5 cm.

*Lateral branches*.—Aspect, primary: About 68° from main trunk axis. Aspect, secondary: About 50° to 60° from primary branch axis. Length, primary: About 80 cm to 120 cm. Diameter, primary: About 8 mm to 12 mm. Internode length: About 3.5 cm. Strength: Strong. Texture, developing branches: Smooth, glabrous. Texture, mature branches: Woody. Color, developing branches: Close to 144A becoming closer to 174A with development. Color, mature branches: Close to 197B.

Leaf description:

*Arrangement*.—Opposite, simple.

*Length*.—About 8 cm.

*Width*.—About 3.3 cm.

*Shape*.—Ovate.

*Apex*.—Acuminate.

*Base*.—Obtuse.

*Margin*.—Entire; undulate.

*Texture, upper and lower surfaces*.—Pubescent; leathery.

*Luster, upper surface*.—Glossy.

*Luster, lower surface*.—Non-glossy; glaucous.

*Venation pattern*.—Palmate.

*Color*.—Developing leaves, upper surface: Centers, randomly-shaped sectors, close to 146B and 146C; towards the margins, randomly-shaped sectors, close to 151B. Developing leaves, lower surface: Centers, randomly-shaped sectors, close to 147A and 147B; towards the margins, randomly-shaped sectors, close to 151D. Fully expanded leaves, upper surface: Centers, randomly-shaped sectors, close to 146A, 143A and 143B; towards the margins, randomly-shaped sectors, close to 9A and 151B; venation, similar to lamina colors. Fully expanded leaves, lower surface: Centers, randomly-shaped sectors, close to 191A and 191B; towards the margins, randomly-shaped sectors, close to 153D; venation, similar to lamina colors.

*Petioles*.—Length: About 6 mm. Diameter: About 1.5 mm. Texture, upper and lower surfaces: Smooth, glabrous. Color, upper and lower surfaces: Close to 151B.

Flower description:

*Flower appearance and arrangement*.—Single cruciform flowers; flowers face mostly upright.

*Natural flowering season and flower longevity*.—Plants flower in mid to late June in Japan; flowers last about one week on the plant; flowers not persistent.

*Fragrance*.—None detected.

*Flower diameter* (*not including flower bracts*).—About 1 mm.

*Flower length* (*not including flower bracts*).—About 0.25 mm.

*Flower buds*.—Length: About 5 mm. Diameter: About 5 mm. Shape: Globular. Color: Close to 145A.

*Petals*.—Quantity and arrangement: Four in a single whorl. Length: About 0.5 mm. Width: About 0.5 mm. Shape: Ovate. Apex: Acute. Base: Obtuse, rounded. Margin: Entire. Texture, upper and lower surfaces: Smooth, glabrous. Color: When opening, upper and lower surfaces: Close to 157B, 157C and 142D. Fully opened, upper and lower surfaces: Close to 142D.

*Flower bracts*.—Quantity and arrangement: About four to eight in one or two whorls. Length: About 2 cm. Diameter: About 1.7 cm. Shape: Ovate. Apex: Acute. Base: Obtuse, rounded. Margin: Entire. Texture, upper and lower surfaces: Smooth, glabrous. Color: When opening, upper and lower surfaces: Close to 142B to 142C; towards the margins, close to 157D and 154D. Fully opened, upper and lower surfaces: Close to NN155C to NN155D and 155C.

*Peduncles*.—Length: About 4 cm. Diameter: About 0.6 mm. Strength: Strong. Aspect: Upright. Texture: Smooth, glabrous. Color: Close to 145A.

*Reproductive organs*.—Androecium: Quantity per flower: About four. Filament length: About 0.5 mm.

Filament color: Close to 155C. Anther length: About 0.1 mm. Anther shape: Round; bilateral split. Anther color: Close to 3C. Pollen amount: None observed. Gynoecium: Quantity per flower: One. Pistil length: About 0.3 mm. Style length: About 0.2 mm. Style color: Close to 155C. Stigma shape: Cylindrical. Stigma color: Close to 155C.

*Seeds and fruits*.—Seed and fruit development have not been observed on plants of the new *Cornus*.

Disease & pest resistance: Plants of the new *Cornus* have not been observed to be resistant to specific pathogens and pests common to *Cornus* plants.

Temperature tolerance: Plants of the new *Cornus* have been observed to tolerate high temperatures about 36.5° C. and low temperatures about −9.4° C.

It is claimed:

1. A new and distinct *Cornus* plant named 'Watashi no Ginga' as illustrated and described.

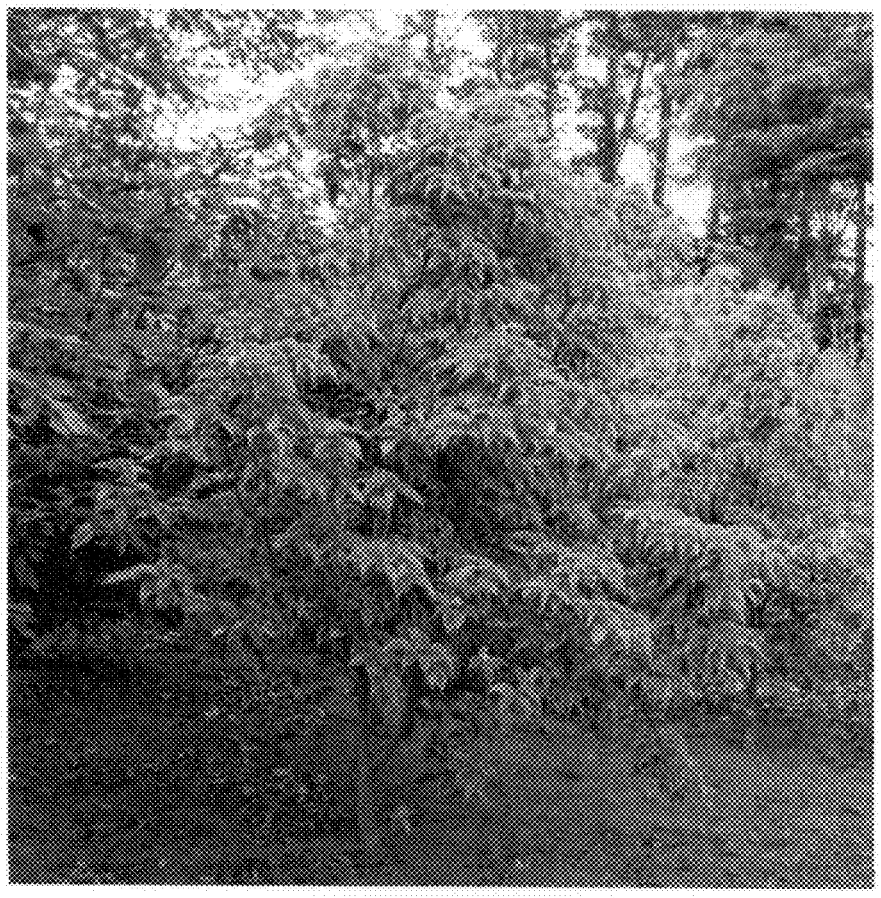

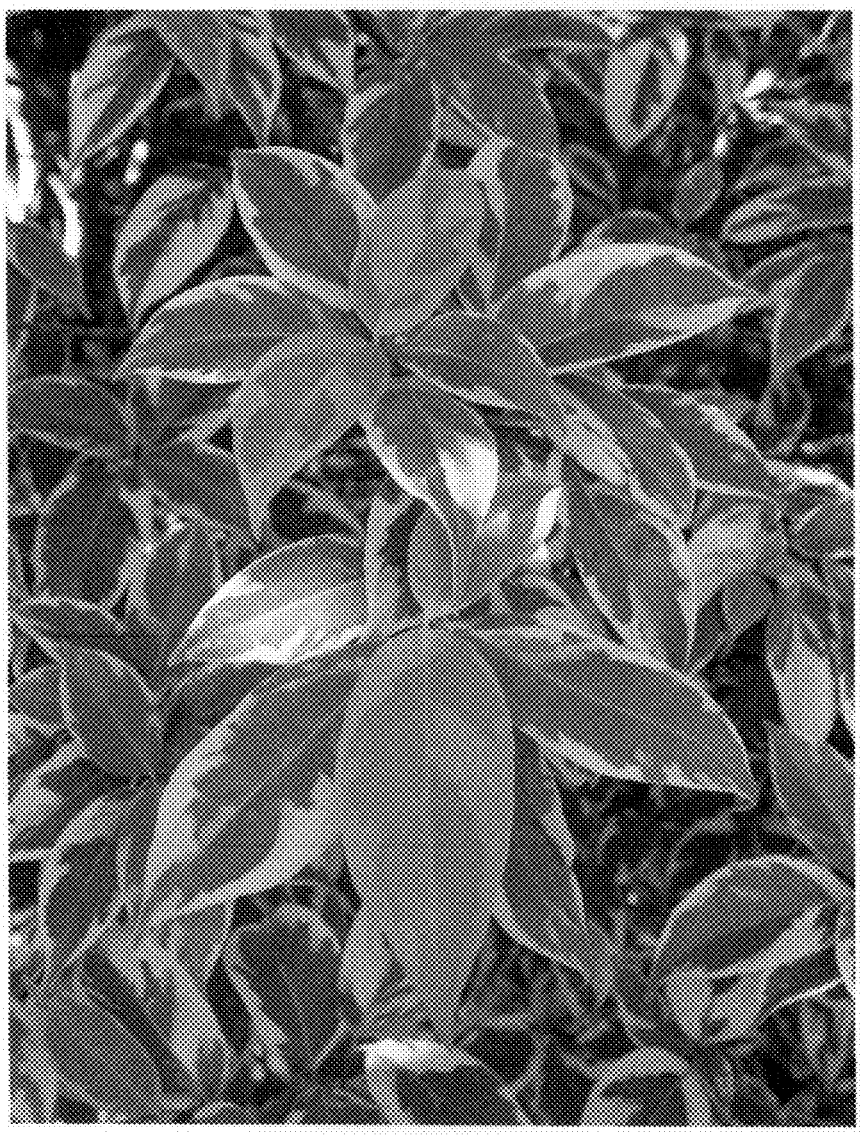

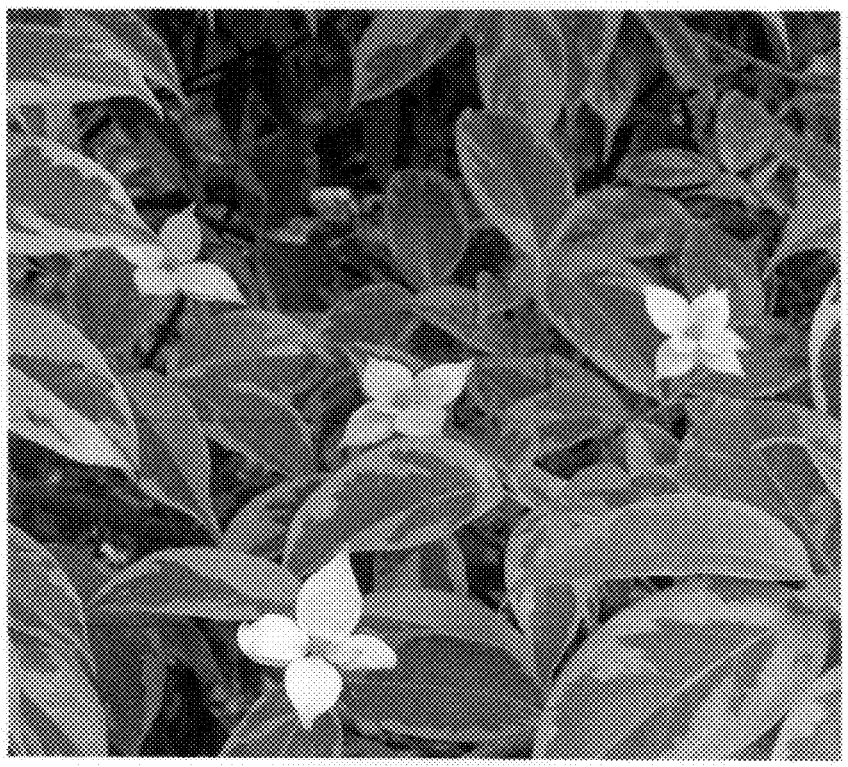

* * * * *